United States Patent [19]
Ogata et al.

[11] 4,435,394
[45] Mar. 6, 1984

[54] 3-SULFONAMIDO-BENZOPHENONIMINE DERIVATIVES USEFUL FOR TREATING VIRUS INFECTIONS

[75] Inventors: Masaru Ogata; Kosaburo Sato, both of Hyogo, Japan

[73] Assignee: Shionogi & Co., Ltd., Osaka, Japan

[21] Appl. No.: 332,099

[22] Filed: Dec. 17, 1981

[51] Int. Cl.³ .................. C07C 143/79; C07C 143/75; A61K 31/18
[52] U.S. Cl. .................................. 424/248.5; 564/99; 564/36; 564/79; 564/82; 564/84; 424/267; 424/274; 424/278; 424/282; 424/283; 424/304; 424/309; 424/300; 424/317; 424/321; 424/323; 260/465 E; 544/159; 546/246; 548/550; 549/350; 549/365; 549/442; 560/27; 560/138

[58] Field of Search ...................... 549/350, 365, 442; 560/27, 138; 424/248.5, 267, 274, 278, 282, 283, 304, 309, 317, 321, 323, 300; 564/79, 84, 99, 36, 82; 260/465 E; 544/159; 546/246; 548/550

[56] References Cited
U.S. PATENT DOCUMENTS
4,160,807 7/1979 Virnig et al. ...................... 423/24

OTHER PUBLICATIONS
Rossi et al., CA 65:10583b, (1966).

Primary Examiner—Thomas A. Waltz
Attorney, Agent, or Firm—Birch, Stewart, Kolasch & Birch

[57] ABSTRACT

3-Sulfonamido-benzophenonimine derivatives useful for prophylactically or therapeutically treating patients suffering from viral infections are provided from 3-sulfonamido-benzophenones.

20 Claims, No Drawings

3-SULFONAMIDO-BENZOPHENONIMINE DERIVATIVES USEFUL FOR TREATING VIRUS INFECTIONS

The present invention relates to 3-sulfonamido-benzophenonimine derivatives being useful as antiviral agents for prophylactically or therapeutically treating patients suffering from viral infections.

BACKGROUND OF THE INVENTION

Certain antifungal 1-dimethylaminosulfonyl-2-aminobenzimidazole compounds have been disclosed in U.S. Pat. No. 3,853,908, and another antiviral 1-sulfonyl-2-amino(or acylamino)benzimidazoles is disclosed in Brit. Pat. No. 1,562,812. Further, a series of diphenylthioureas are active against polio, coxsackie B and echo viruses [Galabov et al., J.Mex.Chem., 23, 1048 (1980)].

A main object of this invention is to provide novel 3-sulfonamido-benzophenonimine derivatives which can inhibit the growth of viruses such as rhinoviruses, polio viruses, coxsackie viruses, echo virus, and the like.

SUMMARY OF THE INVENTION

This invention is directed to 3-sulfonamido-benzophenonimine derivatives of the formula:

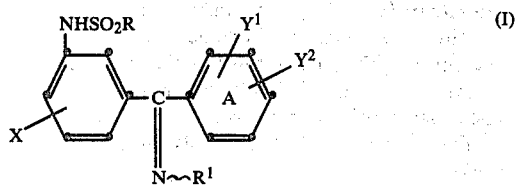

(wherein
R is $C_1$–$C_5$ alkyl, amino, $C_1$–$C_5$ alkylamino, $C_2$–$C_8$ dialkylamino, phenyl, or 5- or 6-membered heterocycle;
$R^1$ is hydroxy, $C_1$–$C_5$ alkoxy, $C_1$–$C_{10}$ acyloxy, benzyloxy, amino, $C_2$–$C_5$ alkoxycarbonylamino, or ureido;
X is hydrogen, $C_1$–$C_5$ alkyl, $C_1$–$C_5$ alkoxy, or halogen;
$Y^1$ and $Y^2$ each is hydrogen, $C_1$–$C_5$ alkyl, $C_1$–$C_5$ alkoxy, $C_1$–$C_5$ alkylthio, $C_2$–$C_5$ alkoxymethyl, $C_2$–$C_5$ alkoxycarbonyl, $C_1$–$C_5$ alkylamino, $C_2$–$C_8$ dialkylamino, $C_1$–$C_5$ alkanesulfonamido, $C_1$–$C_{10}$ acylamino, $C_2$–$C_8$ dialkylaminosulfonylamino, amino, nitro, cyano, hydroxy, or halogen, or
$Y^1$ and $Y^2$, taken together, form $C_1$–$C_3$ alkylenedioxy; and A ring optionally has a condensed benzene ring).

The compounds of formula (I) can be prepared by reacting a 3-sulfonamido-benzophenone of the formula:

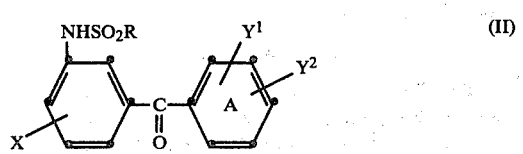

(wherein R, X, $Y^1$, $Y^2$, and A ring each is as defined above) with an amine of the formula:

(wherein $R^1$ is other than $C_1$–$C_{10}$ acyloxy) to give the compounds of formula (I) wherein $R^1$ is other than $C_1$–$C_{10}$ acyloxy, where necessary, followed by acylating the resultant compounds of formula (I) wherein $R^1$ is hydroxyimino to give the compounds of formula (I) wherein $R^1$ is $C_1$–$C_{10}$ acyloxy.

The following definitions refer to the various terms used throughout the disclosure.

The term "$C_1$–$C_5$ alkyl" includes methyl, ethyl, propyl, isopropyl, butyl, isobutyl, sec-butyl, t-butyl, and pentyl.

The term "$C_1$–$C_5$ alkoxy" includes methoxy, ethoxy, propoxy, isopropoxy, butoxy, isobutoxy, and pentyloxy.

The term "$C_1$–$C_5$ alkylthio" includes methylthio, ethylthio, propylthio, isopropylthio, butylthio, isobutylthio, and pentylthio.

The term "$C_2$–$C_5$ alkoxymethyl" includes methoxymethyl, ethoxymethyl, propoxymethyl, isopropoxymethyl, butoxymethyl, isobutoxymethyl, and sec-butoxymethyl.

The term "$C_2$–$C_5$ alkoxycarbonyl" includes methoxycarbonyl, ethoxycarbonyl, propoxycarbonyl, isopropoxycarbonyl, butoxycarbonyl, and isobutoxycarbonyl.

The term "$C_1$–$C_5$ alkylamino" includes methylamino, ethylamino, propylamino, isopropylamino, butylamino, isobutylamino, t-butylamino, and pentylamino.

The term "$C_2$–$C_8$ dialkylamino" includes dimethylamino, methylethylamino, methylpropylamino, diethylamino, ethylpropylamino, dipropylamino, methylbutylamino, and dibutylamino.

The term "$C_1$–$C_5$ alkanesulfonamido" includes methanesulfonamido, ethanesulfonamido, propanesulfonamido, isopropanesulfonamido, butanesulfonamido, isobutanesulfonamido, and pentanesulfonamido.

The term "$C_1$–$C_{10}$ acylamino" includes formylamino, acetylamino, propionylamino, butyrylamino, valerylamino, benzoylamino, phenylacetylamino, phenylpropionylamino, and phenylbutyrylamino.

The term "$C_1$–$C_{10}$ acyloxy" includes formyloxy, acetyloxy, propionyloxy, butyryloxy, valeryloxy, benzoyloxy, phenylacetyloxy, phenylpropionyloxy, and phenylbutyryloxy.

The term "$C_2$–$C_8$ dialkylaminosulfonyl" includes dimethylaminosulfonyl, diethylaminosulfonyl, methylethylaminosulfonyl, methylpropylaminosulfonyl, ethylpropylaminosulfonyl, dipropylaminosulfonyl, methylbutylaminosulfonyl, and dibutylaminosulfonyl.

The term "$C_2$–$C_5$ alkoxycarbonylamino" includes methoxycarbonylamino, ethoxycarbonylamino, propoxycarbonylamino, isopropoxycarbonylamino, butoxycarbonylamino, isobutoxycarbonylamino, sec-butoxycarbonylamino, and t-butoxycarbonylamino.

The term "$C_1$–$C_3$ alkylenedioxy" includes methylenedioxy, ethylenedioxy, and propylenedioxy.

The term "5- or 6-membered heterocycle" includes pyrrolidino, piperidino, and morpholino.

The term "halogen" includes fluorine, chlorine, bromine, and iodine.

The ripple mark means (Z)-form, (E)-form, or a mixture of (Z)-form and (E)-form.

The reaction of 3-sulfonamido-benzophenone (II) with the amine (III) is performed in an appropriate solvent such as methanol, ethanol, tetrahydrofuran, water, dioxane, dimethylformamide, dimethylsulfoxide, or chloroform at a temperature from 30° C. to 200° C., preferably from 50° to 120° C., more preferably at the boiling point of the solvent used.

In the course of the reaction, a mixture of (Z)-form and (E)-form is obtained but can be separated into the respective pure form by crystallization, columnar chromatography, or the like means.

The acylation of the oxime (I, $R^1$=OH) is performed at 0° to 100° C., preferably room temperature to 60° C. in the presence of a base such as triethylamine, pyridine, picolines, or alkali hydroxides in an appropriate solvent such as methylene chloride, chloroform, dimethylformamide, methanol, ethanol, hexamethylphosphoric triamide, or the like.

The starting 3-sulfonamido-benzophenone (II) is prepared by reacting 3-amino-benzophenone of the formula:

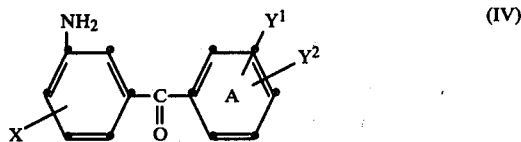

(wherein X, $Y^1$, $Y^2$, and A ring each is as defined above) with a sulfonating agent of the formula:

(wherein A is a reactive group (e.g. halogen) and R is as defined above) in the presence of a base such as triethylamine, pyridine, picolines, or alkali hydroxides in a solvent such as methanol, ethanol, chloroform, methylene chloride, benzene, toluene, or dimethylformamide at a temperature from 0° C. to 160° C., preferably from 15° C. to 100° C.

When the compounds of formula (I) contain any basic moiety such as amino, alkylamino, dialkylamino, or basic heterocycle (e.g. piperidino, morpholino, pyrrolidino, etc.), they can be converted into the pharmaceutically acceptable acid addition salts. Acids to form said salts include inorganic acids such as hydrohalogenic acids, nitric acid, sulfuric acid, or phosphoric acid and organic acids such as acetic acid, citric acid, maleic acid, succinic acid or methanesulfonic acid.

A preferred compound of this invention is represented by the following formula:

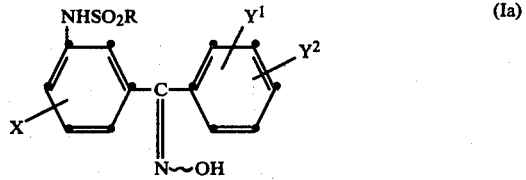

(wherein
R is $C_1$-$C_3$ alkyl, $C_1$-$C_3$ alkylamino, $C_2$-$C_5$ dialkylamino, phenyl, or 5- or 6-membered heterocycle;
X is hydrogen, $C_1$-$C_3$ alkyl, $C_1$-$C_3$ alkoxy, or halogen; and
$Y^1$ and $Y^2$ each is hydrogen, $C_1$-$C_3$ alkyl, $C_1$-$C_3$ alkoxy, $C_1$-$C_3$ alkylthio, $C_2$-$C_4$ alkoxymethyl, amino, nitro, cyano, hydroxy, or halogen).

The compounds of formula (I) illustratively include 3-[N-(dimethylaminosulfonyl)amino]benzophenone oxime;
4'-chloro-3-[N-(dimethylaminosulfonyl)amino]benzophenone oxime;
3-[N-(dimethylaminosulfonyl)amino]-4'-methoxybenzophenone oxime;
3-[N-(dimethylaminosulfonyl)amino]-4'-methylbenzophenone oxime;
2',4'-dimethoxy-3-[N-(dimethylaminosulfonyl)amino]benzophenone oxime;
3-[N-(dimethylaminosulfonyl)amino]-3'-methoxybenzophenone oxime;
3-[N-(dimethylaminosulfonyl)amino]-2'-methoxybenzophenone oxime;
3-[N-(dimethylaminosulfonyl)amino]-4'-methylthiobenzophenone oxime;
3-[N-(dimethylaminosulfonyl)amino]-4'-methoxymethylbenzophenone oxime;
3',4'-dimethoxy-3-[N-(dimethylaminosulfonyl)amino]benzophenone oxime;
3-[N-(dimethylaminosulfonyl)amino]-2'-methylbenzophenone oxime;
3'-amino-3-[N-(dimethylaminosulfonyl)amino]benzophenone oxime;
3-[N-(isopropylaminosulfonyl)amino]-4'-methoxybenzophenone oxime; and
3-[N-(dimethylaminosulfonyl)amino]-4'-hydroxymethylbenzophenone oxime.

Thus-obtained compounds of formula (I) or, if any, their pharmaceutically acceptable acid addition salts are useful as antiviral agents, showing excellent growth inhibitory activities against rhinoviruses, polio viruses, or the like viruses. For example, (E)-3-[N-(dimethylaminosulfonyl)amino]-4'-methoxybenzophenone oxime showed $ED_{50}$ 0.26 γ/ml in the plaque reduction test against polio (type I) virus according to a method similar to Siminoff, Applied Microbiology, 9 (1), 66 (1961).

The compounds of formula (I) or, if any, their pharmaceutically acceptable acid addition salts are enterally or parenterally administered to humans or other animals. The compounds of this invention may be formulated in the preparations for external or internal application in combination with diluents (e.g. starch, sucrose, lactose, calcium carbonate, or kaolin), fillers (e.g. lactose, starch, calcium phosphate, kaolin, bentonite, or talc) lubricants (e.g. stearic acid, sodium benzoate), disintegrators (e.g. starch, agar-agar, carboxymethyl cellulose, or sodium arginate), and other pharmaceutically acceptable excipients.

Such pharmaceutical preparations illustratively include solutions, suspensions, powders, granules, capsules, tablets, dry syrups, injections, suppositories, nose drops, and intranasal sprays. A daily dosage of the compounds of this invention orally administered to humans (e.g. adults) for treating patients suffering from viral infections is 0.1 to 80 mg/kg in single or several divisions, being appropriately controlled depending upon symptoms, case histories, ages, and sex of the patients.

Presently-preferred and practical embodiments of the present invention are illustratively shown in the following examples.

EXAMPLE 1

To a solution of 3-[N-(dimethylaminosulfonyl)-amino]-4'-methoxybenzophenone (9 g) in ethanol (180 ml) is added hydroxylamine hydrochloride (11.23 g), and the resultant mixture is refluxed for 7 hours. The reaction mixture is concentrated in vacuum, and the residue is basified with aqueous sodium hydrogencarbonate and shaken with methylene chloride. The methylene chloride layer is washed with water, dried over anhydrous sodium sulfate and concentrated in vacuum. The residue is chromatographed on a column of silica gel, which is eluted with 20% methanolmethylene chloride. The eluate is concentrated in vacuum to give a crystalline product, which is washed with hot isopropyl ether to give a mixture of (Z)- and (E)-isomers (8.5 g). The mixture is crystallized from ethyl acetateisopropyl ether to give (E)-3-[N-(dimethylaminosulfonyl)-amino]-4'-methoxybenzophenone oxime (1.63 g) as crystals melting at 162° to 164° C.

NMR, δ($d_6$-DMSO): 11.05 (1H), 9.68 (1H), 7.40–6.63 (8H), 3.67 (3H), 2.56 (6H).

The above mother liquor after obtaining (E)-isomer is concentrated in vacuum and the residue is repeatedly recrystallized from benzene and then from ethyl acetateisopropyl ether to give (Z)-3-[N-(dimethylaminosulfonyl)-amino]-4'-methoxybenzophenone oxime (297 mg) as crystals melting at 160.5° to 161° C.

NMR, δ($d_6$-DMSO): 10.87 (1H), 9.66 (1H), 7.37–6.62 (8H), 3.64 (3H), 2.62 (6H).

Absolute configuration of these isomers is determined by X-ray diffraction.

EXAMPLES 2–43

Using the following starting compound (IIa), the reaction is performed as in Example 1, whereby the following product (Ia) is obtained:

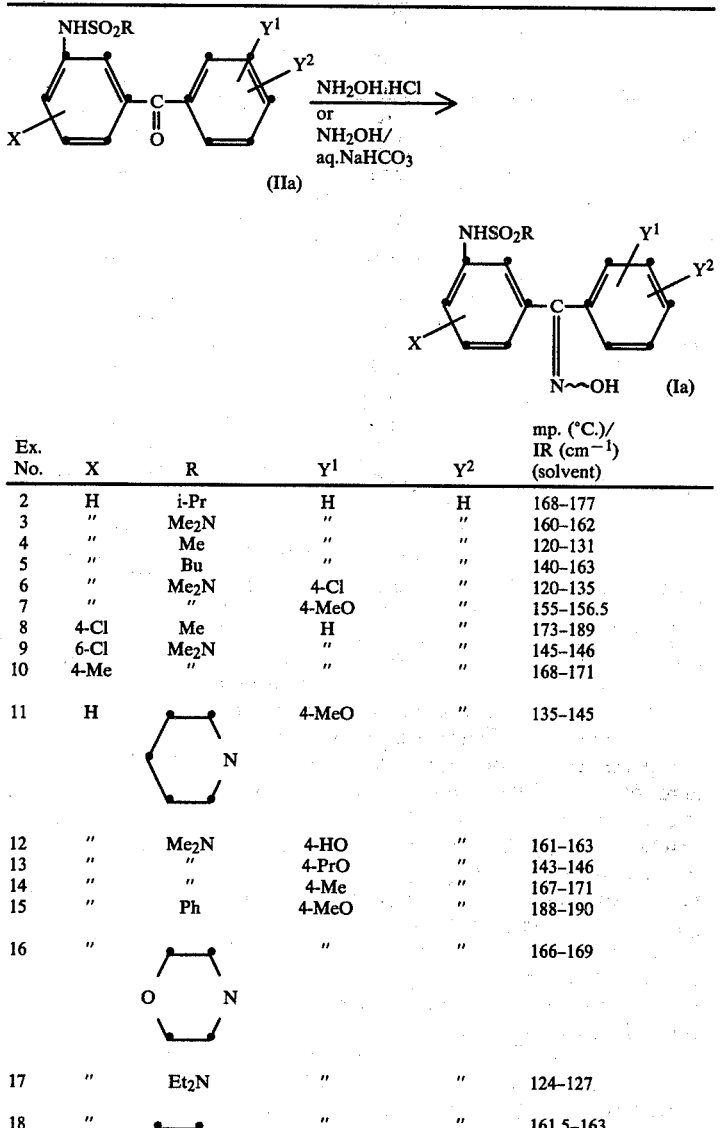

| Ex. No. | X | R | $Y^1$ | $Y^2$ | mp. (°C.)/ IR ($cm^{-1}$) (solvent) |
|---|---|---|---|---|---|
| 2 | H | i-Pr | H | H | 168–177 |
| 3 | " | Me₂N | " | " | 160–162 |
| 4 | " | Me | " | " | 120–131 |
| 5 | " | Bu | " | " | 140–163 |
| 6 | " | Me₂N | 4-Cl | " | 120–135 |
| 7 | " | " | 4-MeO | " | 155–156.5 |
| 8 | 4-Cl | Me | H | " | 173–189 |
| 9 | 6-Cl | Me₂N | " | " | 145–146 |
| 10 | 4-Me | " | " | " | 168–171 |
| 11 | H | piperidino | 4-MeO | " | 135–145 |
| 12 | " | Me₂N | 4-HO | " | 161–163 |
| 13 | " | " | 4-PrO | " | 143–146 |
| 14 | " | " | 4-Me | " | 167–171 |
| 15 | " | Ph | 4-MeO | " | 188–190 |
| 16 | " | morpholino | " | " | 166–169 |
| 17 | " | Et₂N | " | " | 124–127 |
| 18 | " | pyrrolidino | " | " | 161.5–163 |
| 19 | " | Me₂N | " | 2-MeO | 140.5–141.5 |
| 20 | " | " | 4-EtO | H | 158–159 |
| 21 | " | i-Pr | 4-MeO | " | 176–178.5 |
| 22 | " | " | " | 2-MeO | 105–108 |
| 23 | " | Me₂N | 3-MeO | H | 134–136 |
| 24 | " | " | 4-Ph | " | 3570, 3290, 1580.(CHCl₃) |

-continued

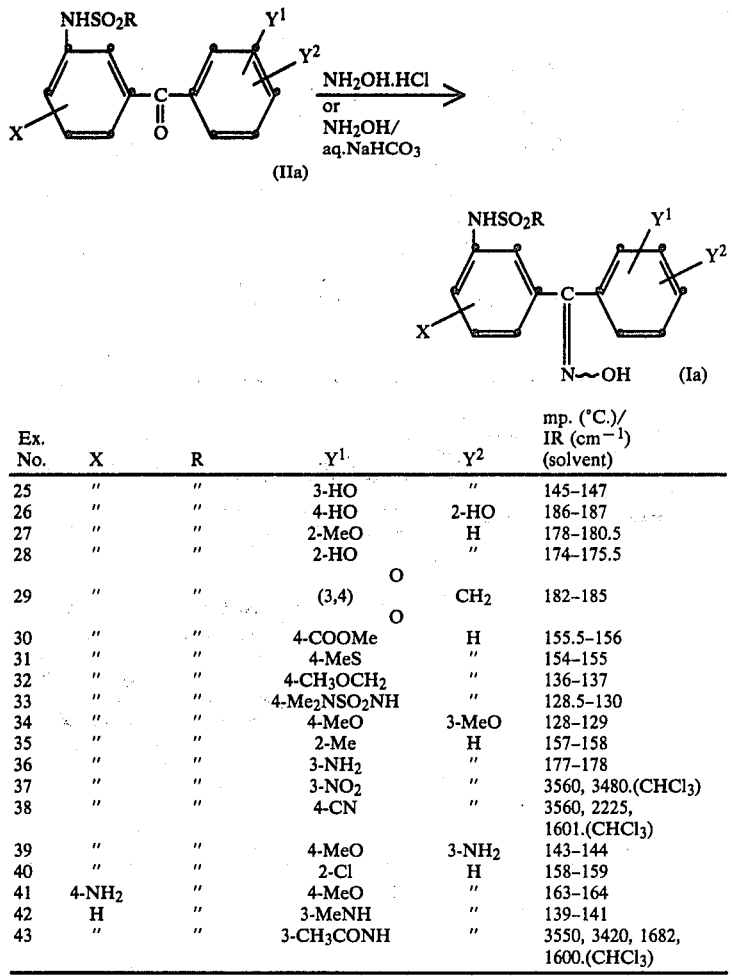

| Ex. No. | X | R | $Y^1$ | $Y^2$ | mp. (°C.)/ IR (cm$^{-1}$) (solvent) |
|---|---|---|---|---|---|
| 25 | " | " | 3-HO | " | 145–147 |
| 26 | " | " | 4-HO | 2-HO | 186–187 |
| 27 | " | " | 2-MeO | H | 178–180.5 |
| 28 | " | " | 2-HO | " | 174–175.5 |
| 29 | " | " | (3,4) O–CH$_2$–O | | 182–185 |
| 30 | " | " | 4-COOMe | H | 155.5–156 |
| 31 | " | " | 4-MeS | " | 154–155 |
| 32 | " | " | 4-CH$_3$OCH$_2$ | " | 136–137 |
| 33 | " | " | 4-Me$_2$NSO$_2$NH | " | 128.5–130 |
| 34 | " | " | 4-MeO | 3-MeO | 128–129 |
| 35 | " | " | 2-Me | H | 157–158 |
| 36 | " | " | 3-NH$_2$ | " | 177–178 |
| 37 | " | " | 3-NO$_2$ | " | 3560, 3480.(CHCl$_3$) |
| 38 | " | " | 4-CN | " | 3560, 2225, 1601.(CHCl$_3$) |
| 39 | " | " | 4-MeO | 3-NH$_2$ | 143–144 |
| 40 | " | " | 2-Cl | H | 158–159 |
| 41 | 4-NH$_2$ | " | 4-MeO | " | 163–164 |
| 42 | H | " | 3-MeNH | " | 139–141 |
| 43 | " | " | 3-CH$_3$CONH | " | 3550, 3420, 1682, 1600.(CHCl$_3$) |

Note:
The abbreviations in the table have the following meanings:
Me (Methyl), Et (Ethyl), Pr (Propyl), Bu (Butyl), Ph (Phenyl), MeO (Methoxy), EtO (Ethoxy), PrO (Propoxy), i- (iso).

EXAMPLE 44

A solution of 3-[N-(dimethylaminosulfonyl)amino]-benzophenone (200 mg) and hydrazine hydrate (100 mg) in ethanol (4 ml) is refluxed for 17.5 hours. The reaction mixture is concentrated in vacuum and the residue is basified with aqueous sodium hydrogencarbonate and shaken with methylene chloride. The organic layer is washed with water, dried over anhydrous sodium sulfate and concentrated in vacuum. The residue is chromatographed on a column of silica gel, which is eluted with 3% methanol and methylene chloride. The eluate is concentrated in vacuum to give 3-[N-(dimethylaminosulfonyl)-amino]benzophenone hydrazone(228 mg) as an oil.
IR(CHCl$_3$): 3380,1600 cm$^{-1}$

EXAMPLE 45

A solution of 3-[N-(dimethylaminosulfonyl)amino]-benzophenone (500 mg) and O-methylhydroxylamine hydrochloride (830 mg) in ethanol (10 ml) is refluxed for 19 hours, and the resultant mixture is concentrated in vacuum. The residue is basified with aqueous sodium hydrogencarbonate and shaken with methylene chloride. The organic layer is washed with water, dried over anhydrous sodium sulfate and concentrated in vacuum. The residue is chromatographed on a column of silica gel, which is eluted with 3% methanol-methylene chloride. The eluate is concentrated in vacuum to give 3-[N-(dimethylaminosulfonyl)amino]benzophenone O-methyloxime (590 mg) as an oil.
IR(CHCl$_3$): 3380,1601 cm$^{-1}$

EXAMPLE 46

A suspension of 3-[N-(dimethylaminosulfonyl)amino]-4'-methoxybenzophenone oxime (1.5 g) and triethylamine (650 mg) in dry methylene chloride (15 ml) is stirred under icy water cooling. A solution of acetyl chloride (337 mg) in dry methylene chloride (3 ml) is dropwise added to the suspension, and 30 minutes later the reaction mixture is mixed with icy water, washed with water, dried over anhydrous sodium sulfate and concentrated in vacuum. The residue is chromatographed on a column of Lobar Lichroprep Si 60, which is eluted with benzene:ethyl acetate (2:1). The eluates from the fraction No. 5–18 are combined and concentrated to give 3-[N-(dimethylaminosulfonyl)amino]-4'-methoxybenzophenone O-acetyloxime (500 mg) as an oil.
IR(CHCl$_3$): 1780 cm$^{-1}$

EXAMPLE 47-8

Using N-methoxycarbonylhydrazine and semicarbaside, the reaction is performed respectively as in Example 45, whereby the following products are obtained:

| Example No. | Compound | mp. (°C.) |
|---|---|---|
| 47 | NHSO$_2$N(CH$_3$)$_2$ ... N NHCOOCH$_3$ | 65-98 |
| 48 | NHSO$_2$N(CH$_3$)$_2$ ... N—NHCONH$_2$ | 219-221 |

EXAMPLES 49-51

The reaction is performed as in Example 1, whereby the following products are obtained:

| Example No. | Compound | mp. (°C.) |
|---|---|---|
| 49 | NHSO$_2$N(CH$_3$)$_2$ ... N—OH | 195.5-198 |
| 50 | NHSO$_2$N(CH$_3$)$_2$ ... N—OH | 188.5-189 |
| 51 | NHSO$_2$N(CH$_3$)$_2$ ... OCH$_3$ ... N—OH | 102-103 dec. (diisopropyl etherate) |

| Example No. | Compound | mp. (°C.) |
|---|---|---|
| 52 | 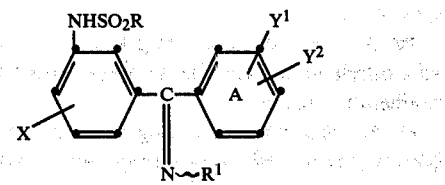 | 194-195 |

What we claim is:

1. 3-Sulfonamido-benzophenonimine derivatives of the formula:

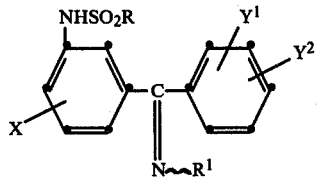

wherein
R is C$_1$-C$_5$ alkyl, amino, C$_1$-C$_5$ alkylamino, C$_2$-C$_8$ dialkylamino, or 5- or 6-membered heterocycle;
R$^1$ is hydroxy, C$_1$-C$_5$ alkoxy, C$_1$-C$_{10}$ acyloxy, benzyloxy, amino, C$_2$-C$_5$ alkoxycarbonylamino, or ureido;
X is hydrogen, C$_1$-C$_5$ alkyl, C$_1$-C$_5$ alkoxy, or halogen;
Y$^1$ and Y$^2$ each is hydrogen, C$_1$-C$_5$ alkyl, C$_1$-C$_5$ alkoxy, C$_1$-C$_5$ alkylthio, C$_2$-C$_5$ alkoxymethyl, C$_2$-C$_5$ alkoxycarbonyl, C$_1$-C$_5$ alkylamino, C$_2$-C$_8$ dialkylamino, C$_1$-C$_5$ alkanesulfonamido, C$_1$-C$_{10}$ acylamino, C$_2$-C$_8$ dialkylaminosulfonylamino, amino, nitro, cyano, hydroxy, or halogen, or
Y$^1$ and Y$^2$, taken together, form C$_1$-C$_3$ alkylenedioxy; and A ring optionally has a condensed benzene ring or a pharmaceutically acceptable acid addition salt thereof.

2. A compound of the formula:

NHSO$_2$R ... Y$^1$ ... Y$^2$ ... X ... N—R$^1$ wherein
R is C$_1$-C$_3$ alkyl, C$_1$-C$_3$ alkylamino, C$_2$-C$_5$ dialkylamino, or 5- or 6-membered heterocycle;
X is hydrogen, C$_1$-C$_3$ alkyl, C$_1$-C$_3$ alkoxy, or halogen; and
Y$^1$ and Y$^2$ each is hydrogen, C$_1$-C$_3$ alkyl, C$_1$-C$_3$ alkoxy, C$_1$-C$_3$ alkylthio, C$_2$-C$_4$ alkoxymethyl, amino, nitro, cyano, hydroxy, or halogen or a pharmaceutically acceptable acid addition salt thereof.

3. A compound according to claim 2, namely 3-[N-(dimethyl-aminosulfonyl)amino]benzophenone oxime.

4. A compound according to claim 2, namely 4'-chloro-3-[N-(dimethylaminosulfonyl)amino]benzophenone oxime.

5. A compound according to claim 2, namely 3-[N-(dimethylaminosulfonyl)amino]-4'-methoxymethylbenzophenone oxime.

6. A compound according to claim 2, namely 3-[N-(dimethylaminosulfonyl)amino]-4'-methylbenzophenone oxime.

7. A compound according to claim 2, namely 2',4'-dimethoxy-3-[N-(dimethylaminosulfonyl)amino]benzophenone oxime.

8. A compound according to claim 2, namely 3-[N-(dimethylaminosulfonyl)amino]-3'-methoxybenzophenone oxime.

9. A compound according to claim 2, namely 3-[N-(dimethylaminosulfonyl)amino]-2'-methoxybenzophenone oxime.

10. A compound according to claim 2, namely 3-[N-(dimethylaminosulfonyl)amino]-4'-methylthiobenzophenone oxime.

11. A compound according to claim 2, namely 3-[N-(dimethylaminosulfonyl)amino]-4'-methoxybenzophenone oxime.

12. A compound according to claim 2, namely 3',4'-dimethoxy-3-[N-(dimethylaminosulfonyl)amino]benzophenone oxime.

13. A compound according to claim 2, namely 3-[N-(dimethylaminosulfonyl)amino]-2'-methylbenzophenone oxime.

14. A compound according to claim 2, namely 3'-amino-3-[N-(dimethylaminosulfonyl)amino]benzophenone oxime.

15. A compound according to claim 2, namely 3-[N-(isopropylaminosulfonyl)amino]-4'-methoxybenzophenone oxime.

16. A compound according to claim 2, namely 3-[N-(dimethylaminosulfonyl)amino]-4'-hydroxymethylbenzophenone oxime.

17. A pharmaceutical composition for treating viral infections comprising an effective antiviral amount of a compound according to claim 1 together with a pharmaceutical carrier, diluent, and/or excipient.

18. A pharmaceutical composition for treating viral infections comprising an effective antiviral amount of a compound according to claim 2 together with a pharmaceutical carrier, diluent, and/or excipient.

19. A method for treating viral infections comprising administering to a host an effective antiviral amount of a compound according to claim 1.

20. A method for treating viral infections comprising administering to a host an effective antiviral amount of a compound according to claim 2.

* * * * *